(12) United States Patent
Muramatsu et al.

(10) Patent No.: US 7,041,118 B2
(45) Date of Patent: May 9, 2006

(54) MULTIFUNCTIONAL SURGICAL OPERATION DEVICE

(75) Inventors: Junichi Muramatsu, Akiruno (JP); Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 477 days.

(21) Appl. No.: 10/103,191

(22) Filed: Mar. 21, 2002

(65) Prior Publication Data

US 2002/0138085 A1    Sep. 26, 2002

(30) Foreign Application Priority Data

Mar. 22, 2001   (JP) ............................. 2001-083708

(51) Int. Cl.
*A61B 17/44* (2006.01)
(52) U.S. Cl. .................. 606/207; 606/208; 606/209
(58) Field of Classification Search .............. 606/139, 606/169, 190, 205, 206, 207, 208, 209, 211, 606/141, 194; 128/831
See application file for complete search history.

(56) References Cited

U.S. PATENT DOCUMENTS 4,869,268 A * 9/1989 Yoon ......................... 128/831
5,474,566 A * 12/1995 Alesi et al. .................. 606/139
5,575,799 A * 11/1996 Bolanos et al. .............. 606/139
6,063,098 A * 5/2000 Houser et al. ............... 606/169
6,371,968 B1 * 4/2002 Kogasaka et al. ........... 606/190

FOREIGN PATENT DOCUMENTS

| DE | 195 37 897 A1 | 3/1997 |
| DE | 102 11 049 A1 | 10/2002 |
| EP | 0 701 797 A2 | 3/1996 |
| EP | 1 002 499 A2 | 5/2000 |
| JP | 2000-152942 | 6/2000 |

* cited by examiner

*Primary Examiner*—Anhtuan T. Nguyen
*Assistant Examiner*—Charles Sam
(74) *Attorney, Agent, or Firm*—Scully, Scott, Murphy & Presser, P.C.

(57) ABSTRACT

A multifunctional surgical operation device comprises clips serving as a plurality of surgical operation tools, a plurality of manipulating wires interlocked with the plurality of clips, the manipulating wires being capable of independently manipulating the plurality of clips respectively, a manipulating section capable of manipulating the plurality of manipulating wires, and a switch lever capable of being selectively engaged with the plurality of manipulating wires. In this device, the manipulating section is manipulated, thereby making it possible to manipulate only the clip interlocked with the manipulating wire engaged with the switch lever.

13 Claims, 13 Drawing Sheets

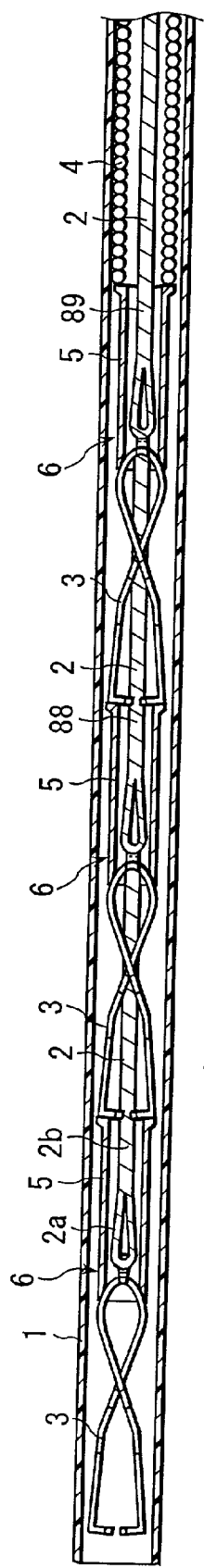
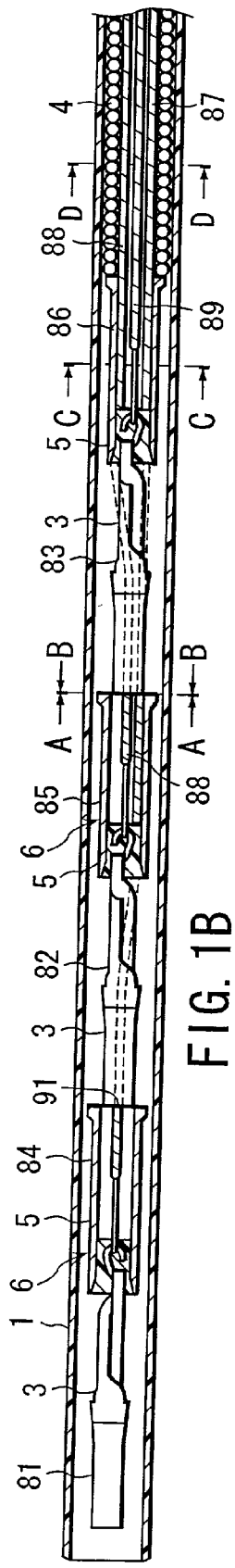
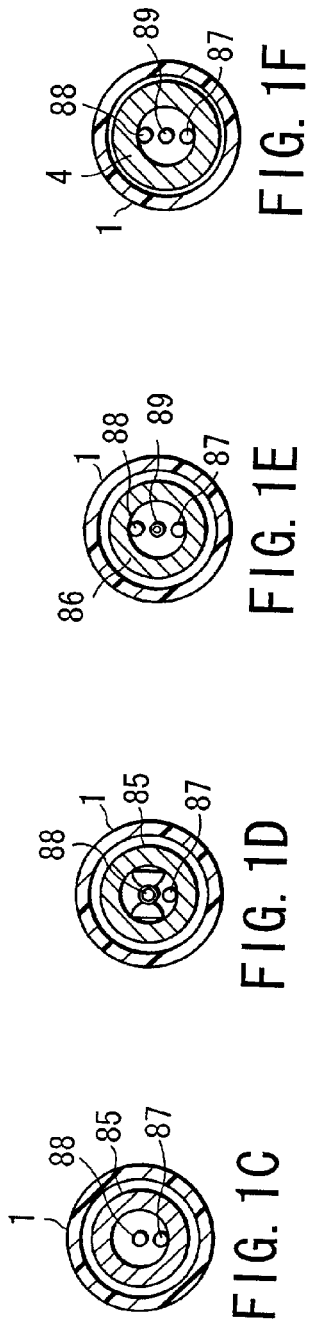
FIG. 1A
FIG. 1B
FIG. 1C
FIG. 1D
FIG. 1E
FIG. 1F

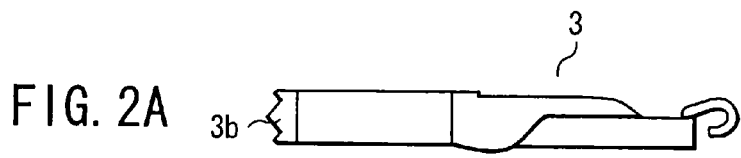
FIG. 2A
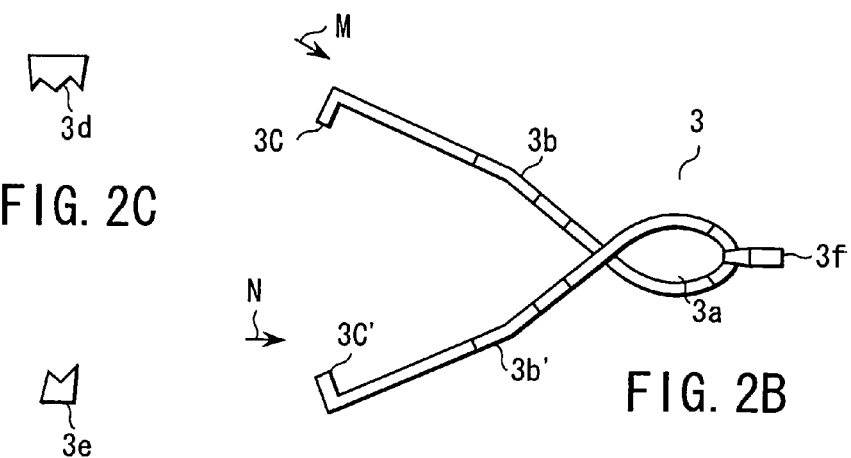
FIG. 2C
FIG. 2B
FIG. 2D
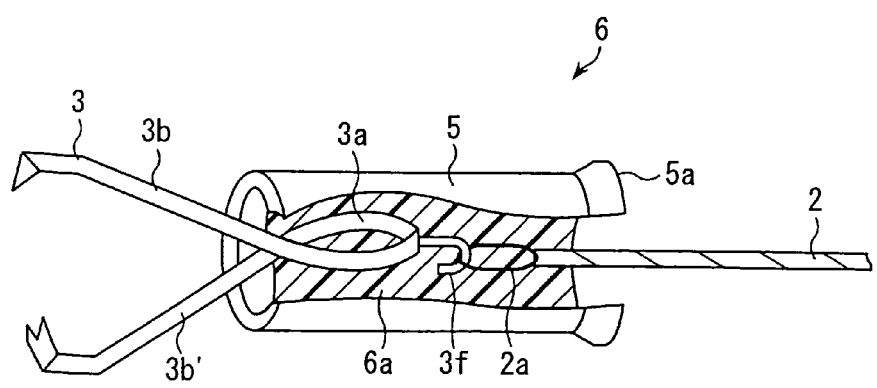
FIG. 3

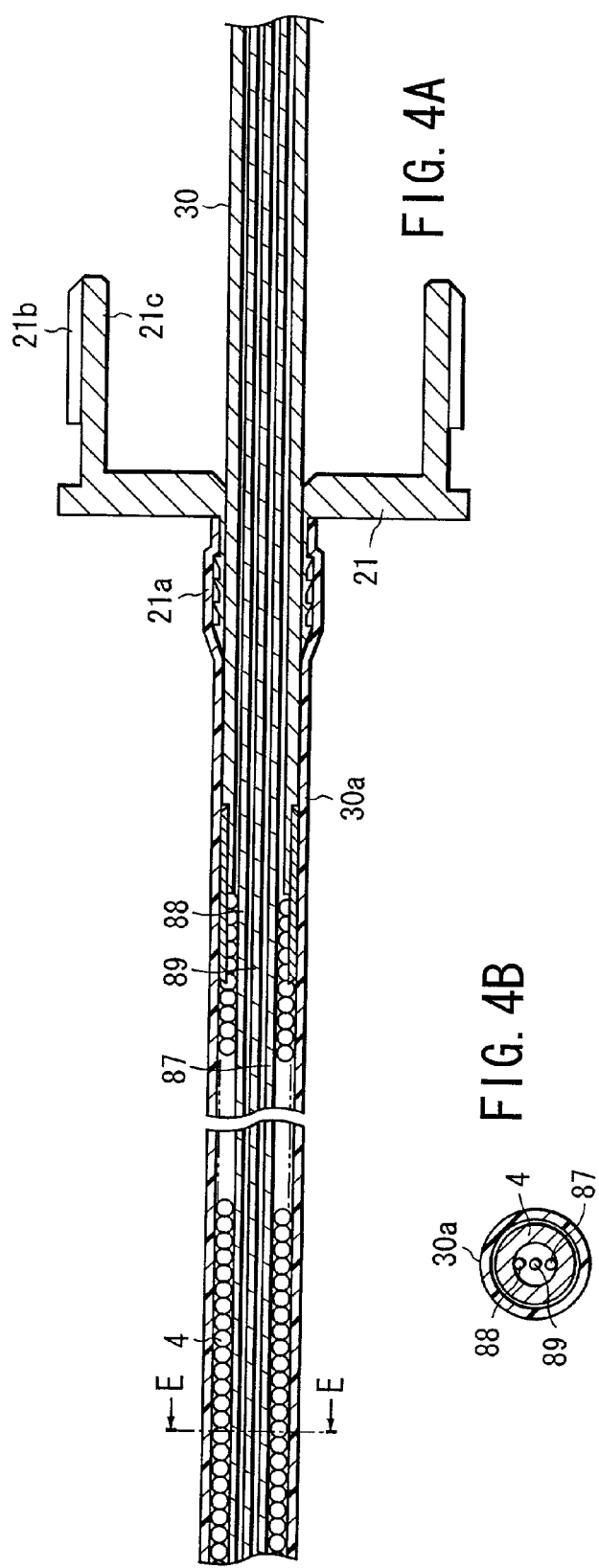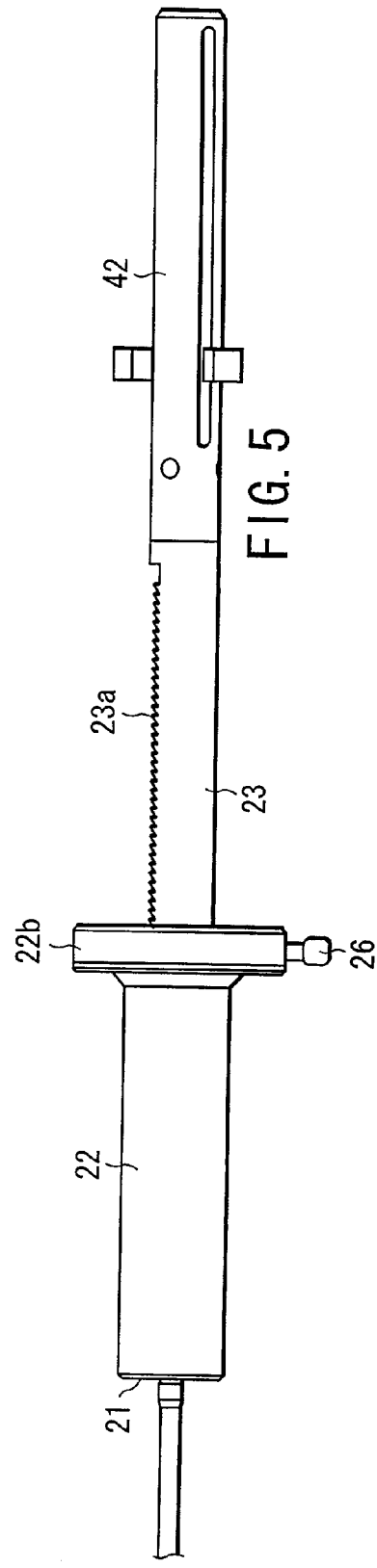

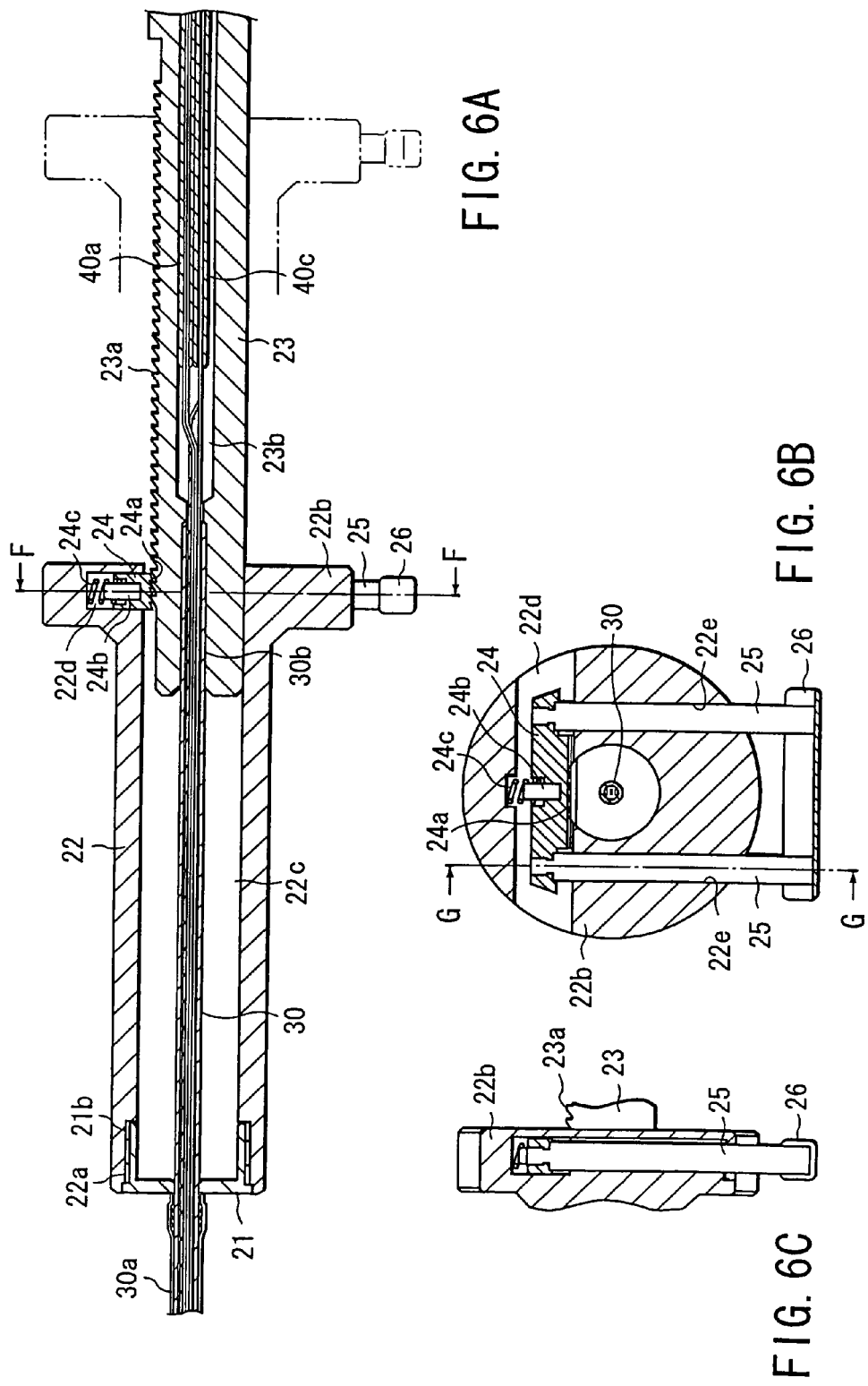

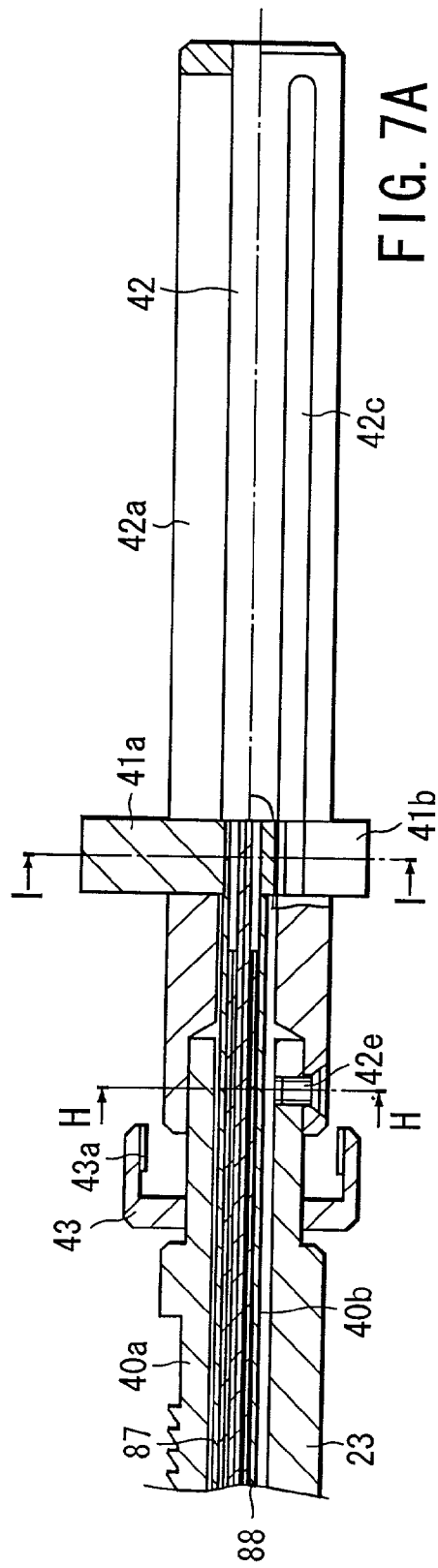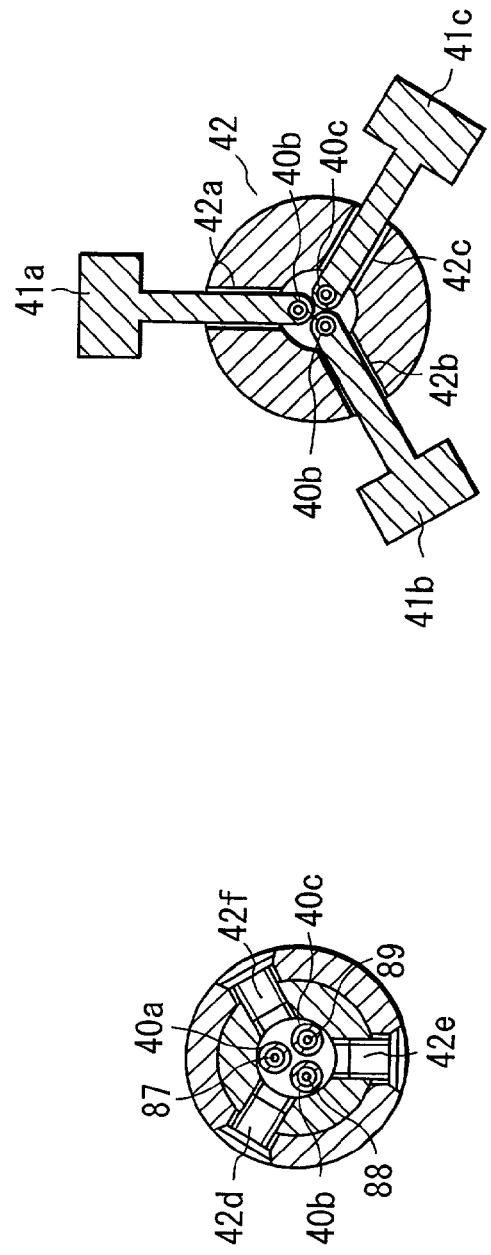

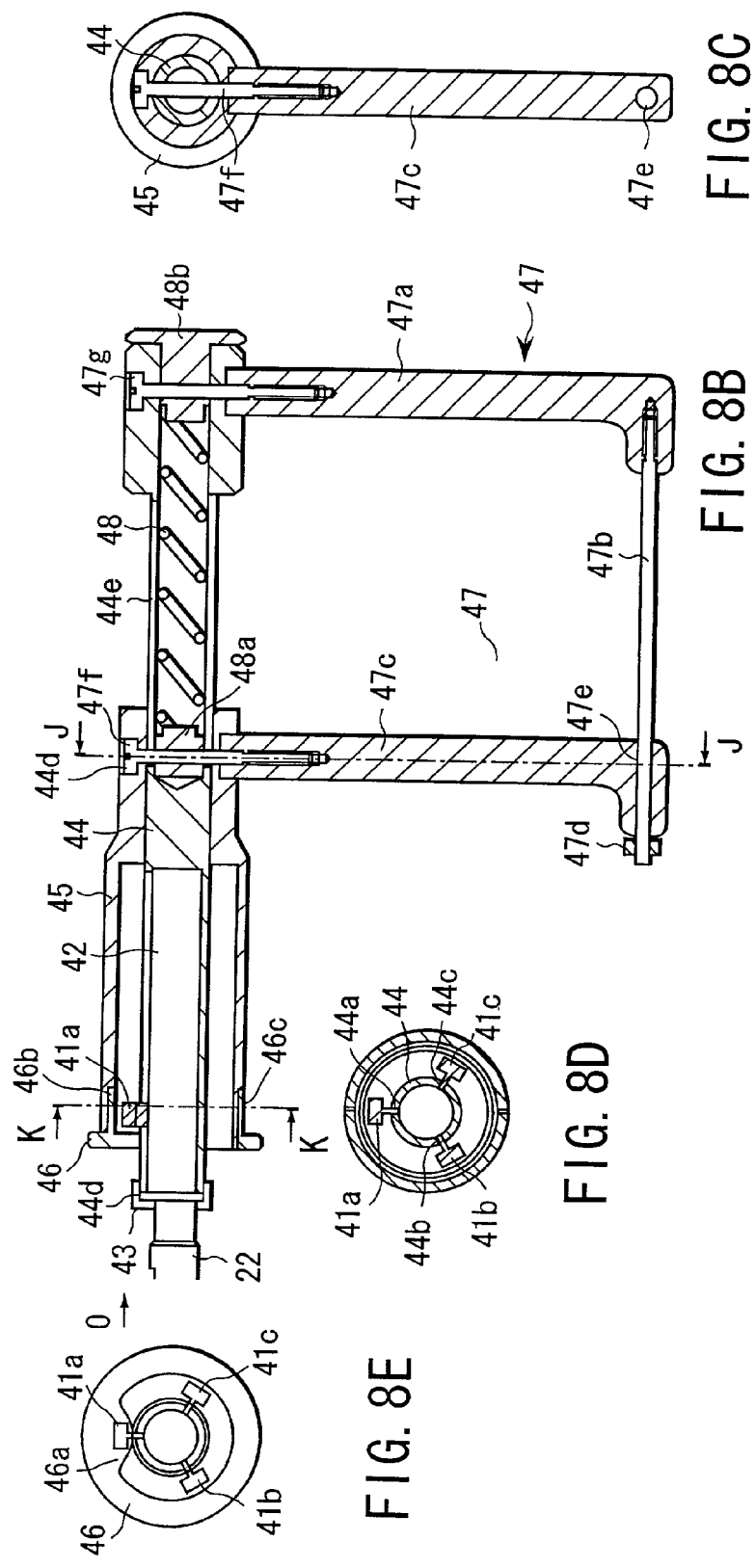

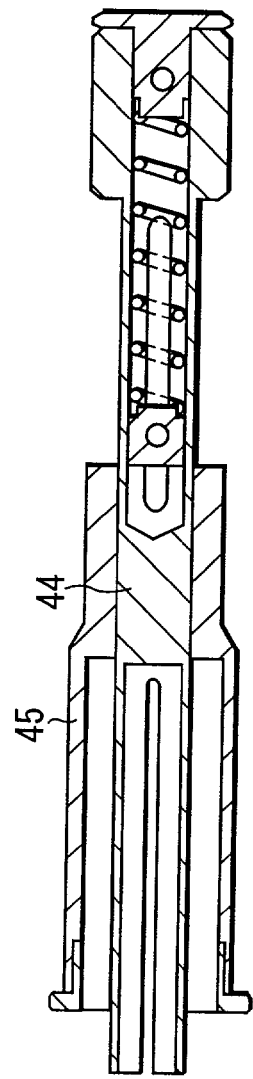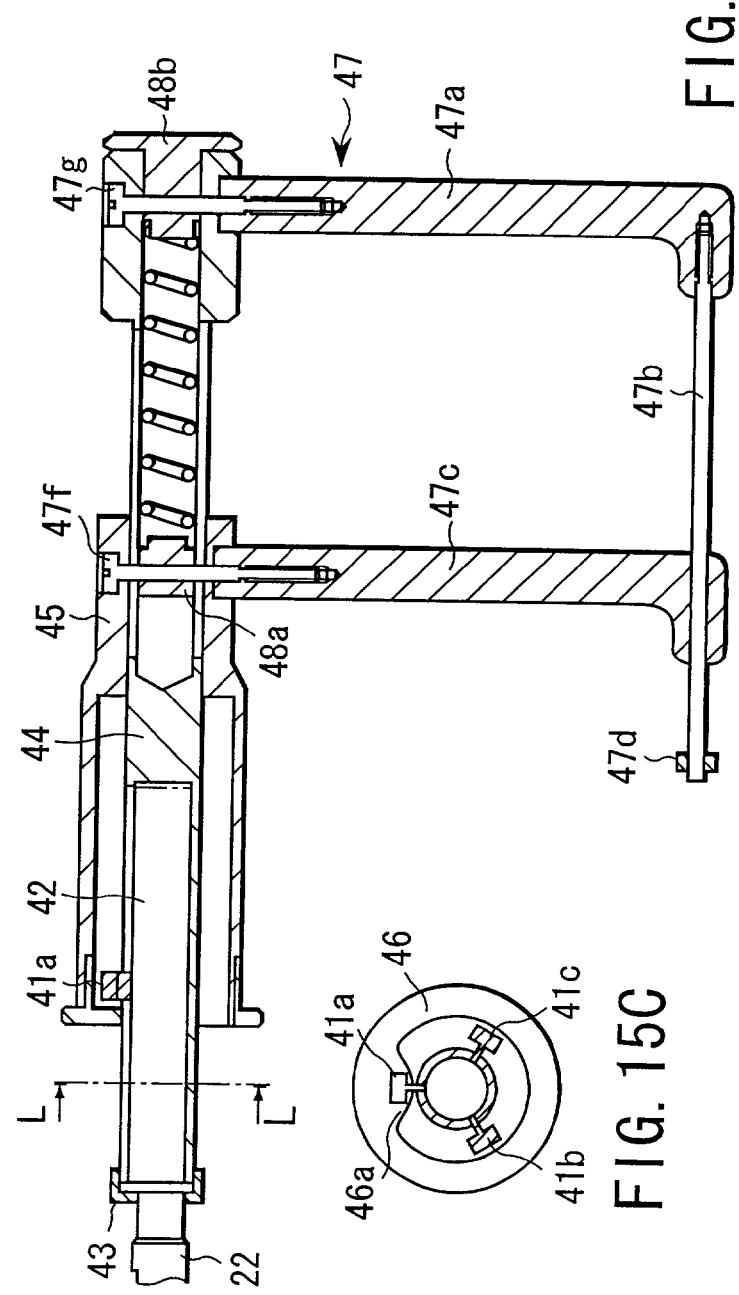

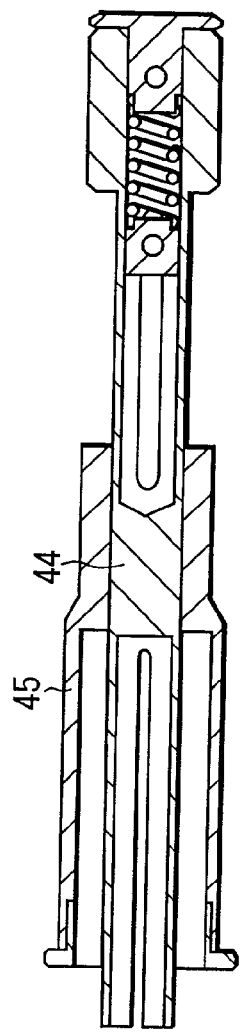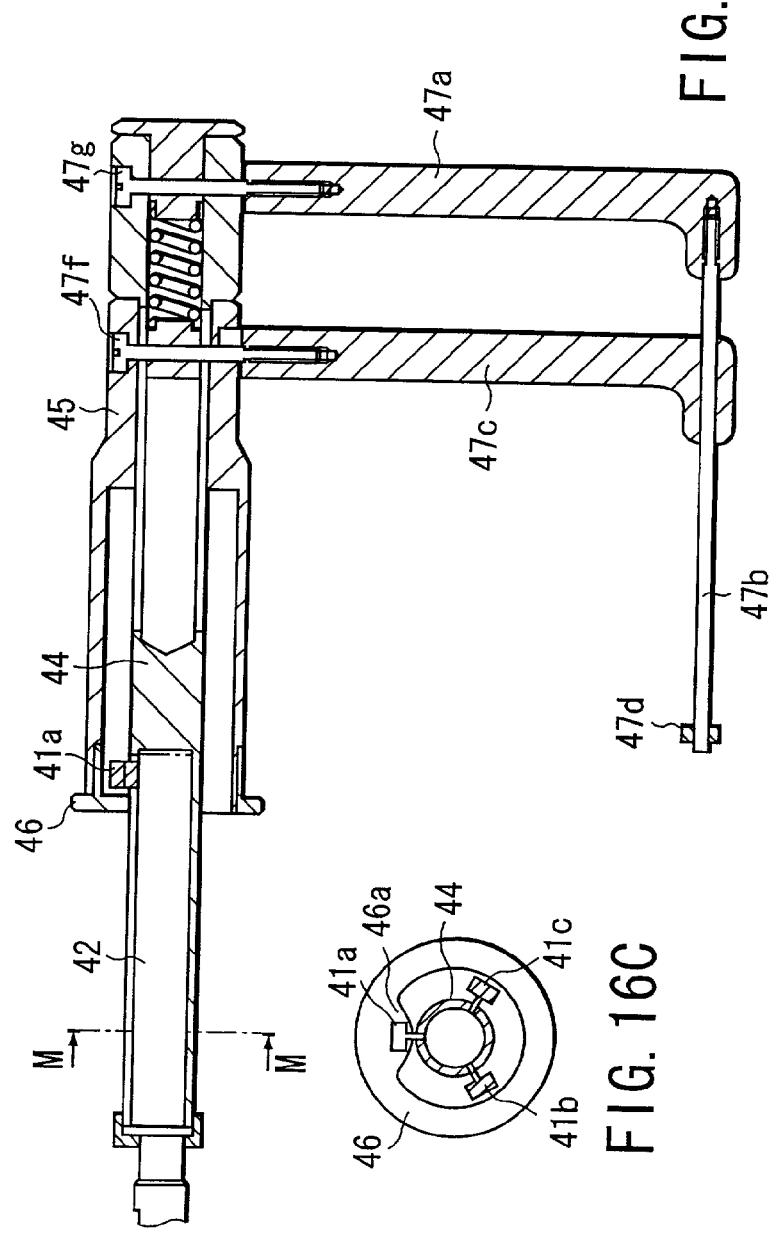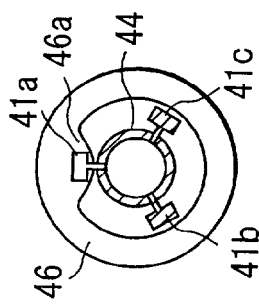

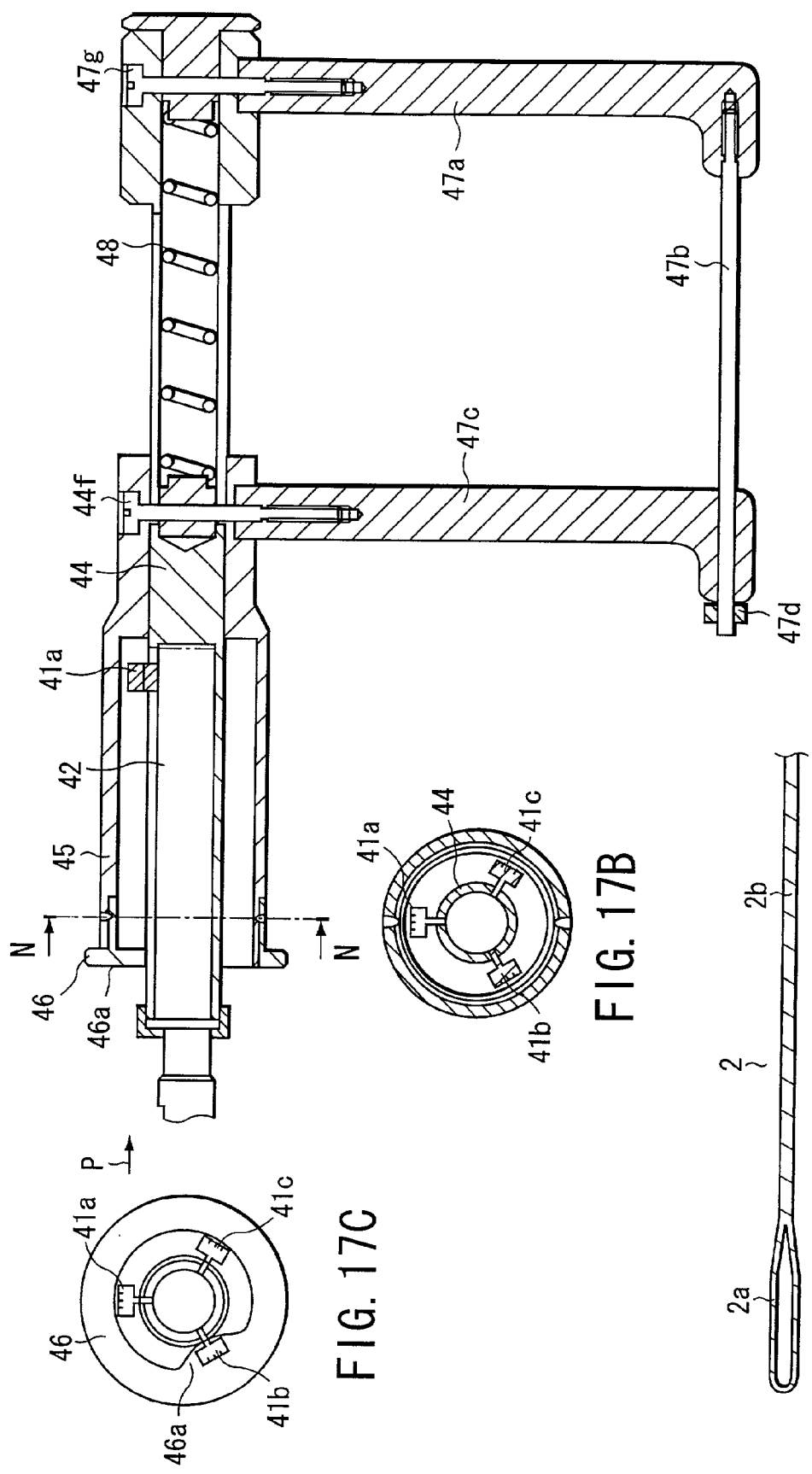

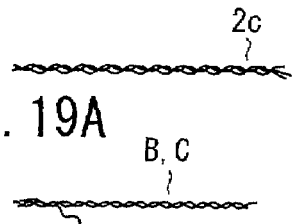
FIG. 19A
FIG. 19B
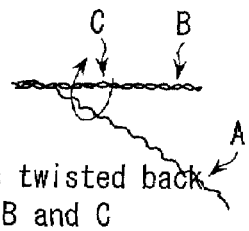
Wire A is twisted back to wires B and C
FIG. 19G
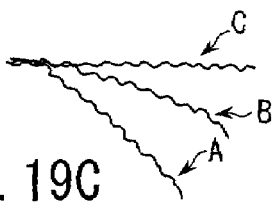
FIG. 19C
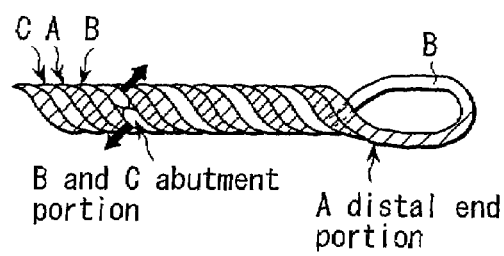
B and C abutment portion    A distal end portion
FIG. 19H
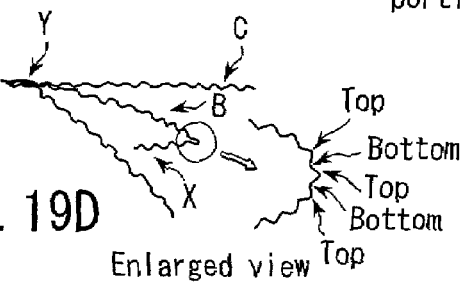
FIG. 19D
Enlarged view
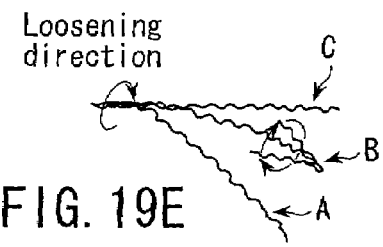
Loosening direction
FIG. 19E
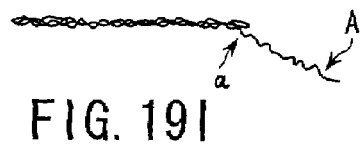
FIG. 19I
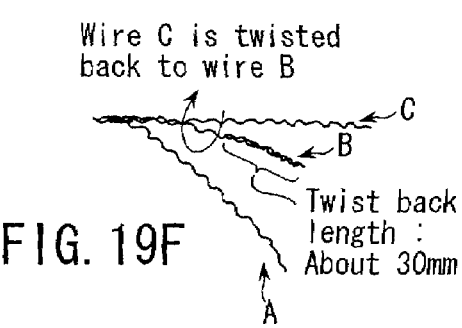
Wire C is twisted back to wire B
Twist back length: About 30mm
FIG. 19F
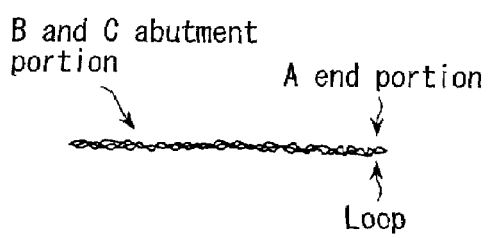
B and C abutment portion    A end portion
Loop
FIG. 19J

MULTIFUNCTIONAL SURGICAL OPERATION DEVICE

CROSS-REFERENCE TO RELATED APPLICATIONS

This application is based upon and claims the benefit of priority from the prior Japanese Patent Application No. 2001-083708, filed Mar. 22, 2001, the entire contents of which are incorporated herein by reference.

BACKGROUND OF THE INVENTION

1. Field of the Invention

The present invention relates to a multifunctional surgical operation device for use in surgical operation.

2. Description of the Related Art

Conventionally, a multifunctional surgical operation device is used in surgical operation. This device is constructed so that a shaft is slidably inserted into a tubular portion and a plurality of surgical operation tools are provided at a distal end portion of the tubular portion and shaft, as disclosed in Jpn. Pat. Appln. KOKAI Publication No. 2000-152942, for example. A plurality of surgical operation tools are thus integrated into one device, thereby making it unnecessary to insert a plurality of devices into a patient or remove them from the patient. Therefore, a surgeon can carry out treatment efficiently by using the multifunctional surgical operation device.

However, a manipulating section of a surgical operation device in which a plurality of surgical operation tools are incorporated into a single device is very complicated. Therefore, use of this device has been an inefficient work. That is, it is more efficient to repeatedly insert a device having one surgical operation tool into the patient and remove it from the patient. Efficiency obtained by incorporating a plurality of surgical operation tools in a single device has been offset by manipulating such a complicated manipulating section.

In addition, because of its complicated manipulation, it has been difficult for a surgeon to select a desired surgical operation tool from the plurality of surgical operation tools, and then, reliably manipulate it.

BRIEF SUMMARY OF THE INVENTION

The present invention has been made in view of the foregoing circumstance. It is an object of the present invention to provide a multifunctional surgical operation device having a switch lever capable of being selectively engaged with a plurality of manipulating members, the surgical operation device being capable of manipulating only a surgical operation tool interlocked with the manipulating members engaged with the switch lever, and capable of efficiently using a device including a plurality of surgical operation tools without manipulating such a manipulating section.

According to the present invention, there can be provided a multifunctional surgical operation device having:

a plurality of surgical operation tools;

a plurality of manipulating members interlocked with the plurality of surgical operation tools and capable of independently manipulating the plurality of surgical operation tools each;

a manipulating section capable of manipulating the plurality of manipulating members; and a switch lever capable of being selectively engaged with the plurality of manipulating members at the manipulating section, wherein only a surgical operation tool interlocked with the manipulating member engaged with the switch lever can be manipulated by manipulation of the manipulating section.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

FIG. 1A is a longitudinal side section showing a distal end portion of a multifunctional surgical operation device according to one embodiment of the present invention;

FIG. 1B is a transverse plan view showing the same according to the present embodiment;

FIG. 1C is a sectional view taken along the line A—A of FIG. 1B;

FIG. 1D is a sectional view taken along the line B—B of FIG. 1B;

FIG. 1E is a sectional view taken along the line C—C of FIG. 1B;

FIG. 1F is a sectional view taken along the line D—D of FIG. 1B;

FIG. 2A is a plan view showing a clip according to the present embodiment;

FIG. 2B is a side view showing the same according to the present embodiment:

FIG. 2C is a view seen in a direction indicated by the arrow M of FIG. 2B;

FIG. 2D is a view seen in a direction indicated by the arrow N of FIG. 2B;

FIG. 3 is a perspective view showing a partially cutout clip unit according to the present embodiment;

FIG. 4A is a longitudinal side view showing a manipulating section according to the present embodiment;

FIG. 4B is a sectional view taken along the line E—E of FIG. 4A;

FIG. 5 is a longitudinal side view showing a manipulating section according to the present embodiment;

FIG. 6A is a longitudinal side view showing a manipulating section according to the present embodiment;

FIG. 6B is a sectional view taken along the line F—F of FIG. 6A;

FIG. 6C is a sectional view taken along the line G—G of FIG. 6A;

FIG. 7A is a longitudinal side view showing a manipulating section according to the present embodiment;

FIG. 7B is a sectional view taken along the line H—H of FIG. 7A;

FIG. 7C is a sectional view taken along the line I—I of FIG. 7A;

FIG. 8A is a longitudinal plan view showing a manipulating section according to the present embodiment;

FIG. 8B is a longitudinal side view showing a manipulating section according to the present embodiment;

FIG. 8C is a sectional view taken along the line J—J of FIG. 8B;

FIG. 8D is a sectional view taken along the line K—K of FIG. 8B;

FIG. 8E is a sectional view seen in a direction indicated by the arrow 0 of FIG. 8B;

FIG. 15A is a plan view showing a manipulating section according to the present embodiment;

FIG. 15B is a longitudinal side section showing a manipulating section according to the present embodiment;

FIG. 15C is a sectional view taken along the line L—L of FIG. 15B;

FIG. 16A is a plan view showing a manipulating section according to the present embodiment;

FIG. 16B is a longitudinal side section showing a manipulating section according to the present embodiment;

FIG. 16C is a sectional view taken along the line M—M of FIG. 16B;

FIG. 17A is a longitudinal side view showing a manipulating section according to the present embodiment;

FIG. 17B is a sectional view taken along the line N—N of FIG. 17A;

FIG. 17C is a side view seen in a direction indicated by the arrow P of FIG. 17A;

FIG. 18 is a side view showing a manipulating wire according to the present embodiment; and FIG. 19A to FIG. 19J are views each illustrating a method for manufacturing a manipulating wire.

DETAILED DESCRIPTION OF THE INVENTION

Figure 9:
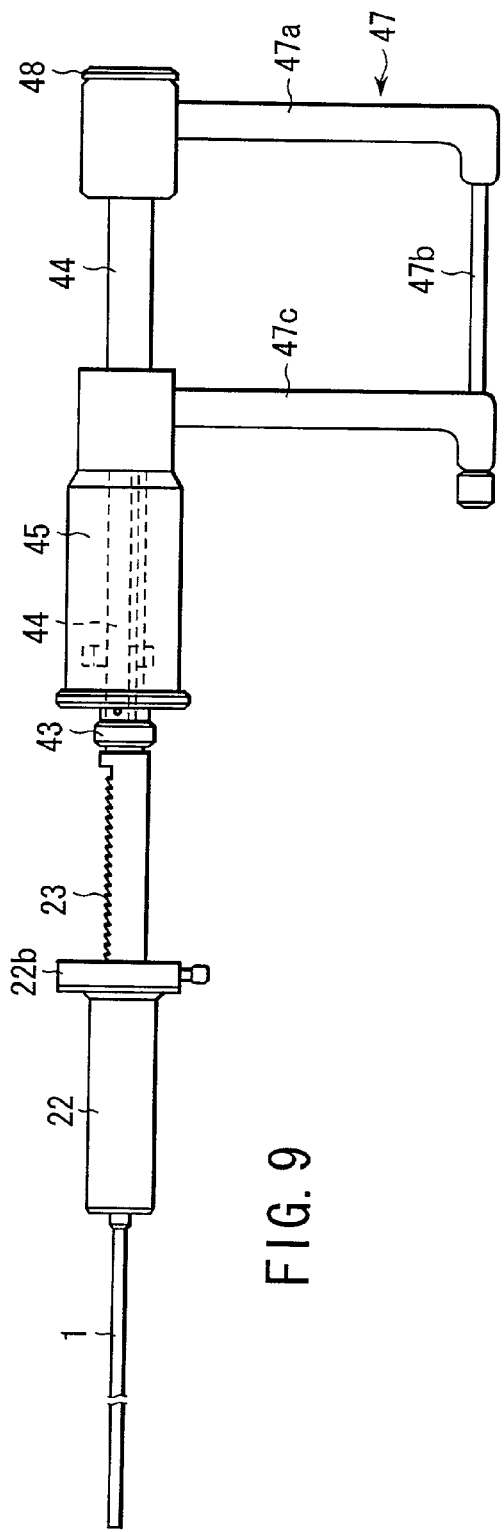
FIG. 9 is a side view showing the entire multifunctional surgical operation device according to the present embodiment.

Hereinafter, preferred embodiments of the present invention will be described with reference to the accompanying drawings.

FIG. 1A to FIG. 1F each show a distal end portion of a multifunctional surgical operation device. An introducing tube 1 has flexibility such that the tube can be inserted into an endoscope channel, and a plurality of manipulating wires 2 serving as manipulating members are movably inserted into this introducing tube 1. A plurality of clips 3 serving as surgical operation tools that are freely protruded and recessed from the distal end portion of the introducing tube 1 are removably connected to the distal end portion of this manipulating wire 2.

The introducing tube 1 is formed of a tube sheath made of a polymeric resin (such as synthetic polyamide, high density/low density polyethylene, polyester, polytetrafluoro ethylene, tetrafluoro ethylene-perfluoroalkylvinyl ether copolymer, or teterafluoro ethylene-hexafluoro propylene copolymer). In this case, the internal and external faces of the sheath have slipping properties, thus making it easy to insert or remove the tube into or from an endoscope channel, protrude the clip 3, and insert the manipulating wire 2.

In addition, the introducing tube 1 is provided as a double tube having an inner layer and an outer layer at a wall section, and may be a tube sheath in which a reinforce member interposing between the double tubes is embedded. In this case, the inner layer and outer layer are formed of the polymeric resin. The reinforce member is formed of a cylindrical blade knitted with a thin metal wire in a lattice shape. In this manner, even if a force of compressing a sheath at the distal end portion and proximal end portion of the sheath is applied, the tube sheath has excellent compression resistance, as compared with a tube sheath in which no reinforce member is embedded, and does not break.

Dimensionally, the introducing tube 1 has an outer diameter such that the tube can be inserted into the endoscope channel. The thickness of the sheath is determined depending on the rigidity of the element material. Although a polymeric resin-based tube is about 0.2 mm to 0.5 mm in diameter, the thickness can be reduced by embedding the reinforce member.

FIG. 2A to FIG. 2D each show a clip 3. In this clip 3, a metallic thin band plate is bent at a center portion, and such a bent portion is defined as a proximal end portion 3a. Both arm sections 3b and 3b' extending from this proximal end portion 3a are crossed each other, and the proximal end portion 3a is formed in a substantially oval shape.

Further, the distal end rim portions of the arm sections 3b and 3b' each are bend to face to each other, and these portions are defined as pinch sections 3c and 3c'. One of the distal ends of the pinch sections 3c and 3c' is formed in a protrusive shape 3d, and the other is formed in a recess shape 3e so as to easily pinch a living tissue. Then, opening/expanding properties are imparted to the arm sections 3b and 3b' so as to open the pinch section 3c. A backwardly protruded hook 3f is mounted on a proximal end portion 3a. At this hook 3f, a stainless based thin plate extending from the proximal end portion 3a is bent in a substantially J shape.

A thin band plate of the clip 3 is made of stainless having resilience to be rigid and capable of reliably pinching a living tissue.

For example, as an ultra-elastic alloy such as nickel-titanium alloy, expanding/opening properties are imparted to the arm sections 3b and 3b', whereby the arm sections 3b and 3b' open more reliably than when the arm sections are protruded from the sheath.

If a tensile stress quantity of about 2 kg to 5 kg is applied to a hook 3f provided at the proximal end portion of the clip 3, the hook 3f cannot be maintained in the J shape, is deformed, and extends in a substantially I shape.

In addition, the band plate of the clip 3 is 0.15 mm to 0.3 mm in thickness; the pinch sections 3c and 3c' are 0.5 mm to 1.2 mm in plate width; and the arm sections 3b and 3b' are 0.5 mm to 1.5 mm in plate width. The proximal end portion 3a is 0.3 mm to 0.5 mm in plate width. The hook 3f is protruded with a length of about 1 mm to 5 mm from a proximal end portion 3a of the clip 3.

The manipulating wire 2 consists of a loop wire 2a and a proximal end wire 2b as shown in FIG. 1A. A closed loop wire 2a is molded at a distal end of a proximal end wire 2b composed of a twisted metallic wire. In order to form the loop wire 2a, as described later, the loop wire 2a is formed of a single twisted wire of the proximal end wire 2b, and then, the proximal end wire 2b is twisted back again. In this way, the loop can be molded at a bonding section of the loop wire 2a and proximal end wire 2b without interposing specific bonding parts and providing a hard portion.

Thus, an outer diameter of a bonding section of the loop wire 2a and proximal end wire 2b does not increase. As described later, in the case where a plurality of clips 3 are mounted in the introducing tube 1, a clearance in the introducing tube 1 is very small, and thus, use of the present embodiment is effective.

The manipulating wire 2 is provided as a stainless-based twisted wire, for example. Such a twisted wire is more flexible than a single wire, and the flexibility of the introducing tube 1 is not degraded. A force of 2 kg to 5 kg is applied to the loop wire 2a when the clip 3 is ligated. At this time, it is required to set dimensions so that the loop wire 2a does not break.

In addition, the manipulating wire 2 may be coated with a polymeric resin with its good slipping properties such as a high density/low density polyethylene, for example. The thickness of the coat is optimally about 0.05 mm to 0.1 mm. When the slipping properties of the manipulating wire 2 is thus improved, the slide resistance in the manipulating member described later can be decreased, thus making it possible to reduce the force quantity during ligation. The proximal end wire 2b is 0.3 mm to 0.6 mm in outer diameter, and the loop wire 2a is 0.1 mm or more in diameter.

Further, as shown in FIG. 1A, a protruding member 4 is inserted into the introducing tube 1. The protruding member 4 has flexibility such that the member can be inserted into the introducing tube 1. This protruding member is disposed backwardly of the clip tightening ring 5 described later, the ring being mounted in the introducing tube 1, so as to directly receive a force applied by the manipulating wire 2 when the clip 3 is ligated.

This protruding member 4 is provided as a coil sheath with its irregular internal and external faces on which a metallic wire whose sectional face is rounded (such as stainless wire) is closely wound. This protruding member 4 is moved to the distal end side relevant to the introducing tube 1, thereby making it possible to protrude the clip 3 and clip tightening ring 5 from the introducing tube 1.

The protruding member 4 may be provided as a rectangular coil sheath with its flat internal and external faces obtained after the wire cross section is made rectangular by breaking a metallic wire (such as stainless wire) whose sectional face is rounded, and then the wire with its rectangular sectional face is closely wound on the sheath. Dimensionally, this rectangular coil sheath can be provided as a coil sheath with its large inner diameter even if the element wire diameter of the same wire is used as compared with the rounded shaped coil sheath.

Further, the protruding member 4 may be a tube sheath made of a polymeric resin, for example, (such as synthetic polyamide, high density/low density polyethylene, polyester, polytetrafluoro ethylene, tetrafluoro ethylene perfluoroalkylvinyl ether copolymer, or teterafluoro ethylenehexafluoro propylene copolymer). The tube sheath has slipping properties on its outer and inner faces, thereby making it easy to be inserted into the introducing tube 1 and to insert the manipulating wire 2.

In addition, for example, a tube sheath in which a metallic wire (such as stainless wire) is embedded in a polymeric resin-based tube sheath may be provided. This sheath has high resistance, as compared with a tube sheath in which no wire is embedded, and does not break.

The protruding member 4 has an outer diameter such that the member can be inserted into the introducing tube 1 and an inner diameter such that the manipulating wire 2 can be inserted. The outer diameter is 3 mm or less in diameter, and the inner diameter is as large as possible. However, the thickness is required such that the protruding force quantity can be reliably transmitted, and the sheath does not break even if a force is applied when the clip 3 is ligated.

In addition, the clip tightening ring 5 engagingly mounted on the clip 3 is constructed as shown in FIG. 3. This clip tightening ring 5 is engagingly mounted on the arm sections 3b and 3b' of the clip 3 to close the arm sections 3b and 3b' of the clip, and is formed in a substantially tubular shape. The clip 3 and manipulating wire 2 are engaged with each other by being hooked by a hook 3f of the loop wire 2a.

The proximal end portion 5a of the clip tightening ring 5 is molded in accordance with a bending angle of the clip pinch sections 3c and 3c' so that the pinch sections 3c and 3c' abut against the proximal end portion 5a of the clip tightening ring 5 reliably. In this manner, even if a compression force is applied between the clip 3 and protruding member 4, the clip 3 and clip tightening ring 5 are not inclined, and the applied compression force can be reliably transmitted to its distal end.

This clip tightening ring 5 is molded by injection-molding of a rigid resin (such as polybutyl telephthalate, polyamide, polyphenyl amide, liquid crystal polymer, polyether ketone, polyphthal amide), or alternatively, injection-molding, cut processing, and plastic processing of a metal (such as stainless), for example.

Figure 12:
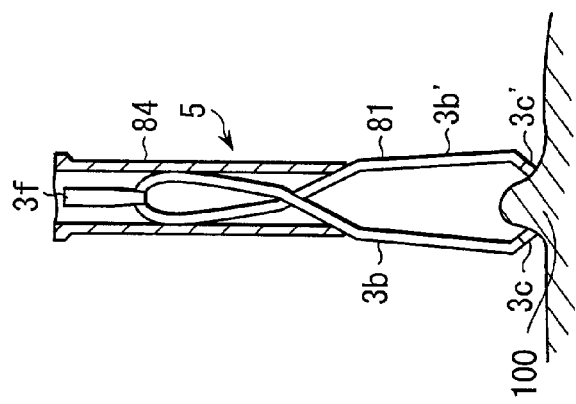
FIG. 12 is a longitudinal side section showing a state in which a clip is retained in a living tissue according to the present embodiment.

In addition, the clip tightening ring 5 is 0.6 mm to 1.3 mm in inner diameter, is about 1.0 mm to 2.5 mm in outer diameter, and is about 4 mm to 8 mm in length. As shown in FIG. 12, when the clip 3 is ligated, even if the hook 3f provided at the proximal end portion of the clip 3 is deformed, it is required to set a length such that the clip does not fly out of the clip tightening ring 5.

The clip 3 is engagingly mounted in the clip tightening ring 5, and a clip unit 6 is formed. In addition, a loop wire 2a at the distal end portion of the manipulating wire 2 is engaged with the hook 3f provided at the proximal end portion 3a of the clip 3. A polymeric material 6a such as silicone is engaged in the clip tightening ring 5 so as not to easily disengage the clip tightening ring 5 from the clip 3 and the hook 3f from the loop wire 3a.

Parts constructed as described previously are incorporated in the introducing tube 1, as shown in FIG. 1A and FIG. 1B. That is, in the introducing tube 1, three clip units 6 are disposed to be arranged in series. However, the number of clip units 6 is not limited to three in series, and many more clip units 6 may be mounted in the introducing tube 1.

For clarity, the clip units 6 mounted in the introducing tube 1 are named as follows. A clip 81, clip 82, and clip 83 are defined in order from the clip 3 mounted at the most distal end. Clip tightening rings 6 on which the clips 81, 82, and 83 are engagingly mounted respectively are defined as clip tightening rings 84, 85, and 86. Manipulating wires 2 engaged with the clips 81, 82, and 83 respectively in the clip tightening rings 84, 85, and 86 are defined as manipulating wires 87, 88, and 89.

A protruding member 4 is inserted backwardly of the clip tightening ring 86. The manipulating wire 87 is inserted in order into a gap 91 between a pinch section of the clip 82 and a clip tightening ring 85, and then, a gap 92 between a pinch section of the clip 83 and the clip tightening clip 86, and is inserted into the proximal end side of the protruding member 4. In addition, the manipulating wire 88 is inserted into the gap 92 between the pinch section of the clip 83 and the clip tightening ring 86, and is inserted into the proximal end side of the protruding member 4. On the other hand, the manipulating wire 89 is guided into an internal cavity of the protruding member 4 intact, and is inserted into the proximal end portion of the protruding member 4. That is, in the protruding member 4, three manipulating wires 87, 88, and 89 are inserted to be arranged in parallel to each other.

Now, a construction of a manipulating section provided at the proximal end side of the introducing tube 1 will be described here with reference to FIG. 4A to FIG. 4C.

As shown in FIG. 4A and FIG. 4B, an introducing tube connecting member 21 is formed in a substantially cylindrical shape, and a cylindrical protrusion portion 21a is provided at its distal end portion. This protrusion portion 21a is fixed to be press-fitted to the proximal end portion of the polymeric resin-based introducing tube 1, and a connecting cylinder body 21c having a male screw portion 21b on its outer periphery face is provided at its rear end portion.

As shown in FIG. 5, a female screw section 22a provided at the distal end portion of a substantially cylindrical introducing tube slider 22 is connected to be screwed at a male screw section 21b of the introducing tube connecting member 21. A jaw section 22b is provided at the proximal end portion of this introducing tube slider 22.

The introducing tube slider 22 has a cylindrical internal cavity 22c. A manipulating member slider 23 is inserted into this internal cavity 22c. The manipulating member slider 23 is formed in a substantially cylindrical shape, and a ratchet 23a is provided at a part of the outer periphery face in an axial direction. This manipulating slider 23 is movably engaged into an internal cavity 22c provided at the introducing tube slider 22.

A claw engaging recess portion 22d is provided at the inner periphery portion located at the jaw section 22b of the introducing tube slider 22, and a claw member 24 is housed in this claw engaging recess portion 22d. The claw member 24 is provided as a substantially rectangular member, and a claw 24a capable of being engaged with the ratchet 23a of the manipulating member slider 23 is provided at its distal end portion.

A pin 24b is protruded at the intermediate portion at the rear end portion of the claw member 24, and a spring 24c engaged with the pin 24b is provided inside of a claw engaging recess portion 22d. Then, the claw member 24 is biased in the direction of the ratchet 23a by the spring 24c.

Further, two through holes 22e are punched at the opposite side of the claw member 24 of the jaw section 22b of the introducing tube slider 22, and a rod 25 is movably engaged into these two holes 22e. The distal end portion of the rod 25 is fixed to the claw member 24, and a button 26 is provided at the proximal end portion.

When this button 26 is pushed in the direction of the introducing tube slider 22, the pushing force is transmitted to the claw member 24 via the rod 25, and the spring 24c is pushed and contracted. In this manner, the claw member 24 is disengaged from the ratchet 23a provided at the manipulating member slider 23 so that the introducing tube slider 22 can move on the manipulating member slider 23 in an axial direction.

Further, as shown in FIG. 4A, FIG. 4B, and FIG. 6A to FIG. 6C, a cylindrical protecting pipe 30 is engaged with the proximal end portion of the protruding member 4, and a distal end portion 30a of the protecting pipe 30 is welded at the proximal end portion of the protruding member 4. A proximal end portion 30b of the protecting pipe 30 is bonded with the distal end portion of the manipulating member slider 23. Three manipulating wires 87, 88, and 89 guided from the internal cavity of the protruding member 4 are guided into the internal cavity of the protecting pipe 30 intact, and are inserted into the internal cavity 23b of the manipulating member slider 23. The protecting pipe 30 is provided for the purpose of preventing slackness of the manipulating wires 87, 88, and 89 and easily sliding the manipulating member slider 23 in the internal cavity 22c of the introducing tube slider 22.

As shown in FIG. 7A to FIG. 7C, manipulating pipes 40a, 40b, and 40c are welded respectively at the proximal end portions of three manipulating wires 87, 88, and 89 guided into the internal cavity of the manipulating member slider 23. Three knobs 41a, 41b, and 41c are welded at the proximal end portions of the manipulating pipes 40a, 40b, and 40c, and these three knobs 41a, 41b, and 41c are bonded while the knobs are inclined by 120 degrees in the circumferential direction so as not to interfere with each other.

A slider seat 42 is fixed at the proximal end portion of the manipulating member slider 23 by screws 42d, 42e, and 42f. Three slits 42a, 42b, and 42c are provided at the slider seat 42 along the axial direction. These three slits 42a, 42b, and 42c are provided to be inclined in the circumferential direction by 120 degrees. The knobs 41a, 41b, and 41c are engaged into these three slits 42a, 42b, and 42c, respectively, and the respective knobs 41a, 41b, and 41c can slide in the slits 42a, 42b, and 42c independently.

In addition, a joint 43 is mounted rotatably at the proximal end portion of the manipulating member slider 23. At the inner periphery face of the joint 43, a screw 43a is formed so as to enable screwing with the manipulating section 44 described later.

The manipulating section 44 is formed in a substantially cylindrical shape, as shown in FIG. 8A to FIG. 8E, and the slider seat 42 is engaged into the internal cavity of its distal end portion. Three slits 44a, 44b, and 44c provided to be inclined in the circumferential direction by 120 degree are provided in the axial direction of the cylindrical shape of the manipulating section 44. Three knobs 41a, 41b, and 44c engaged in the slider seat 42 can slide on these slits 44a, 44b, and 44c.

A male screw 44d is formed at the distal end portion of the manipulating section 44. This screw is connected to be screwed with a female screw 43a of the joint 43. In this manner, the manipulating section 44, slider seat 42, and manipulating member slider 23 are integrally connected with each other.

A vertically-penetrating cutout portion 44e is provided at the proximal end portion of the manipulating section 44. A sliding bolt 47f slides at this cutout portion 44e described later, whereby the manipulating wire 2 can be retracted.

At the manipulating section 44, a substantially cylindrical manipulating section cover 45 is engaged so as to cover the manipulating section 44. A through hole 44d in which the sliding bold 47f can be engaged is provided at the proximal end portion of the manipulating section cover 45.

A switch lever 46 is provided at the distal end of the manipulating section cover 45. This switch lever 46 is formed in a substantially cylindrical shape, a part of the internal cavity extends to the inside, and a knob engaging portion 46a is formed. Then, the switch lever 46 is mounted rotatably on the manipulating section cover 45 via pins 46b and 46c. The switch lever 46 is rotated by 120 degrees, whereby a knob engaging portion 46a can be engaged with a knob 41a.

Further, as shown in FIG. 8A to FIG. 8E and FIG. 9, a handle 47 is formed in a substantially U shaped. This handle is composed of a fixed handle 47a consisting of a cylinder member, a connecting bar 47b, a sliding handle 47c, and a sliding handle stop tube 47d. The connecting bar 47b is screwed at the proximal end portion of the fixed handle 47a. The other end of the connecting bar 47b is screwed with the sliding handle stop tube 47d via a through hole 47e provided at the proximal end portion of the sliding handle 47c. That is, the sliding handle 47c can freely slide on the connecting bar 47b.

The distal end portion of the fixed handle 47a is fixed to the manipulating member 44 via a fixing bolt 47g. The distal end portion of the sliding handle 47c is fixed to the proximal end portion of the manipulating section cover 45 via a sliding bolt 47f. At this time, the sliding bolt 47f is engaged in the cutout portion 44d provided at the proximal end portion of the manipulating section 44.

In addition, a coil shaped spring 48 is engaged in the internal cavity of the proximal end portion of the manipulating section 44. Both ends of this spring 48 are fixed by spring stops 48a and 48b. The spring 48 applies a force of forwardly biasing the spring stop 48a, and thus, the sliding bolt 47f, manipulating section cover 45, and sliding handle 47c are always biased in a distal end direction.

The spring stop 48a is formed in a substantially cylindrical shape, and has a through hole such that the sliding bolt 47f can be engaged. Then, the sliding bolt 47f is engaged into the internal cavity of the manipulating section 44 so as to apply the biasing force of the spring 48 to the sliding bolt 47f. In addition, the spring stop 48b is formed in a substantially cylindrical shape, and has a through hole such that the fixing bolt 47g can be engaged. Then, the fixing bolt is engaged into the inner cavity of the manipulating portion 44 and abuts against the proximal end portion of the spring 48.

Now, working of a first embodiment will be described here.

As shown in FIG. 1A and FIG. 1B, the introducing tube 1 is inserted into a living body cavity via a forceps channel of an endoscope. At this time, the proximal end portion of the introducing tube 1 is located forwardly of the distal end of a clip 81, and is enveloped in the internal cavity of the introducing tube 1. After the introducing tube 1 has been in close proximity to the vicinity of a target tissue, the jaw section 22b of the introducing tube slider 22 shown in FIG. 9 is pinched, and the introducing tube slider 22 is retracted to the proximal end side. At this time, an endoscopic image is well observed, and it is checked that the arm sections 3b and 3b' of the clip 81 are protruded from the distal end of the introducing tube 1.

Figure 10:
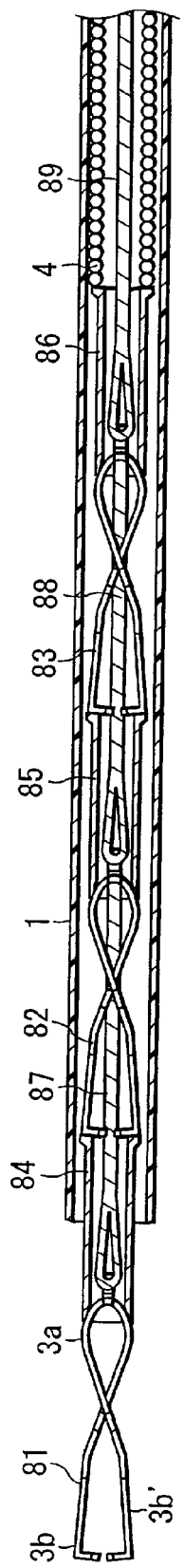
FIG. 10 is a longitudinal side section showing a distal end portion of the device according to the present embodiment.

Further, as shown in FIG. 10, the introducing tube slider 22 is gradually retracted to a location at which the clip tightening ring 5 is protruded from the distal end of the introducing tube 1 by about 1 mm to 5 mm. At this time, care must be taken so that the arm sections 3b and 3b' of the clip 82 are not protruded from the distal end of the introducing tube 1. This is because, if the arm sections 3b and 3b' of the clip 82 are protruded, there is no means for controlling the clip 81, thus making it very difficult to reliably ligate the target living tissue.

When the introducing tube slider 22 is retracted, the claw member 24 is always in engagement with the ratchet 23a of the manipulating member slider 23 by a biasing force of the spring 24c. Therefore, even if a hand is released from the introducing tube slider 22 at one point, the introducing tube slider 22 does not move on the manipulating member slider 23.

In addition, although the introducing tube slider 22 can move when a force is applied in the traction direction, the claw member 24 and ratchet 23a are engaged with each other so as to disable movement even if such a force is applied in the distal end direction of the introducing tube 1. If the introducing tube slider 22 is excessively retracted, the claw member 24 and ratchet 23a may be disengaged from each other by pressing a button 26. When the button 26 is pressed in the direction of the jaw section 22b, the applied force is transmitted to the claw member 24 via a rod 25, the spring 24c is deformed after being compressed. Then, the claw member 24 and ratchet 23a are disengaged from each other.

Figure 11:
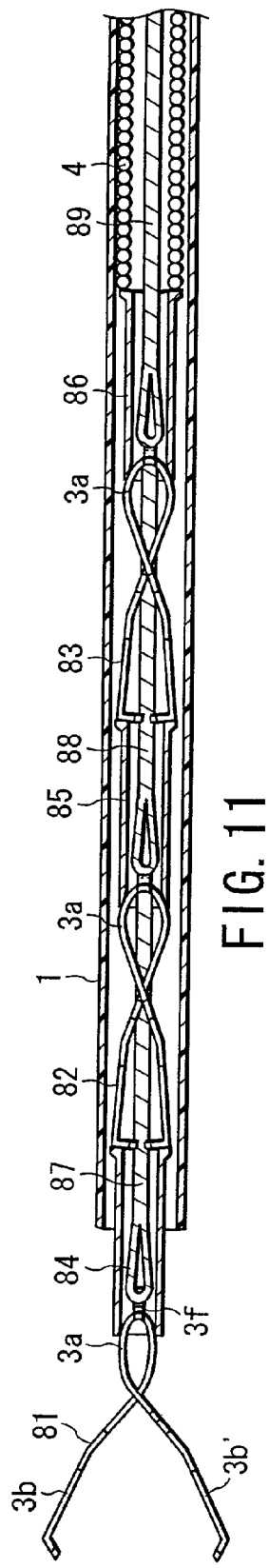
FIG. 11 is a longitudinal side section showing a distal end portion of the device according to the present embodiment.

While the clip 81 and clip tightening ring 84 are protruded from the introducing tube 1, when a manipulating wire 87 is retracted, the force applied by the manipulating wire 87 is transmitted to the clip 81. The protruding member 4 is fixed, and thus, the applied force acts as a compression force between the clip 81 and protruding member 4. Due to this compression force, an oval portion of the proximal end portion 3a of the clip 81 is retracted into the clip tightening ring 84. Dimensionally, the oval portion of the proximal end portion 3a is greater than the internal diameter of the clip tightening ring 84, and the oval portion is crushed by the clip tightening ring 84. Then, the arm sections 3b and 3b' expand/open significantly to the outside, as shown in FIG. 11.

The compression force acts to the clips 82 and 83 as well as the clip 81. The clips 82 and 82 are not retracted into the clip tightening rings 85 and 86 respectively, and the arm sections 3b and 3b' do not expand or open significantly. That is, the clip 82 and clip tightening ring 85 and the clip 83 and clip tightening ring 86 act as a hard connecting member provided between the clip 81 and protruding member 4. Then, the compression force is applied between the clip 81 and protruding member 4, and is received there.

The clips 82 and 83 are not retracted into the clip tightening rings 85 and 86 because the arm sections 3b and 3b' do not expand or open more than the internal diameter of the introducing tube 1. That is, even if the compression force acts to the clips 82 and 83, the expansion/opening of the arm sections 3b and 3b' stops when these arms abut against the inner wall of the introducing tube 1. These arms do not expand or open any more. Thus, the oval portion does not contract at the proximal end portion 3a, and is not retracted into the clip tightening ring 5.

While the arm sections 3b and 3b' of the clip 81 expand/open, the introducing tube 1 is guided so as to push the pinch sections 3c and 3c' against a target living tissue 100. The manipulating wire 87 is further retracted, whereby the arm sections 3b and 3b' of the clip 81 are retracted into the clip tightening ring 84, and the pinch sections 3c and 3c' of the clip 81 are closed. While the living tissue 100 is reliably pinched between pinch sections 3c and 3c' of the clip 81, the manipulating wire 87 is further retracted, and the hook 3f is extended, whereby the clip 81 and manipulating wire 87 are disengaged from each other. In this manner, as shown in FIG. 12, the clip 81 can be retained in a body cavity while the living tissue 100 is pinched.

Figure 13:
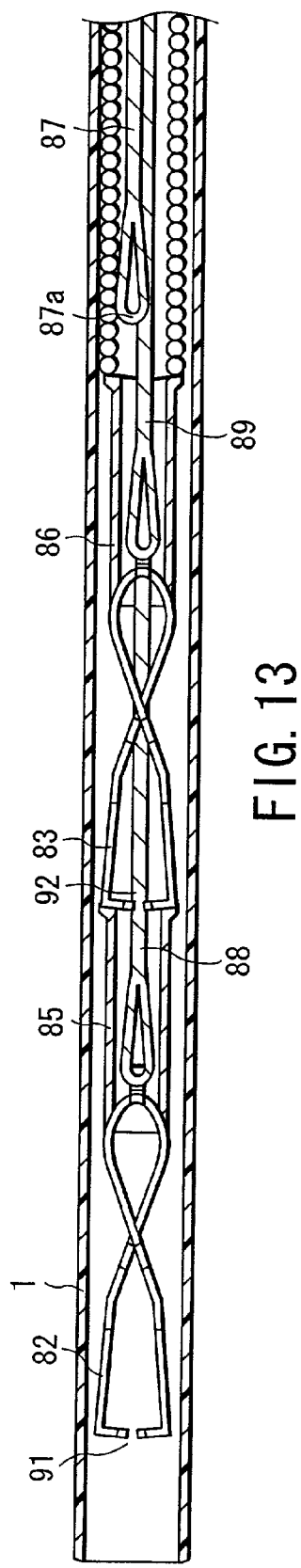
FIG. 13 is a longitudinal side section showing a distal end portion of the device according to the present embodiment.

In order to continuously retain the clip 82 in the living tissue in a body cavity, the manipulating wire 87 separated from the clip 81 is refracted to the internal cavity of the protruding member 4, as shown in FIG. 13. That is, the distal end of the manipulating wire 87 passes through a gap 91 between the pinch sections 3c and 3c' of the clip 82, the inside of the clip tightening ring 85, and then, a gap 92 between the pinch sections 3c and 3c' of the clip 83 in order and the inside of the clip tightening ring 86, and reaches the internal cavity of the protruding member 4. The manipulating wire 87 separated from the clip 81 is thus retracted, whereby preparation for ligating the clip 82 has completed. In this state, the introducing tube 1 is retracted to the proximal end side, and the clip 82 and clip tightening ring 85 are protruded from the distal end of the introducing tube 1.

A manipulation for ligating the clip 82 is completely identical to that for retaining the clip 81 in the living tissue 100. This makes it possible to retain the clip 82 in the living tissue.

Figure 14:
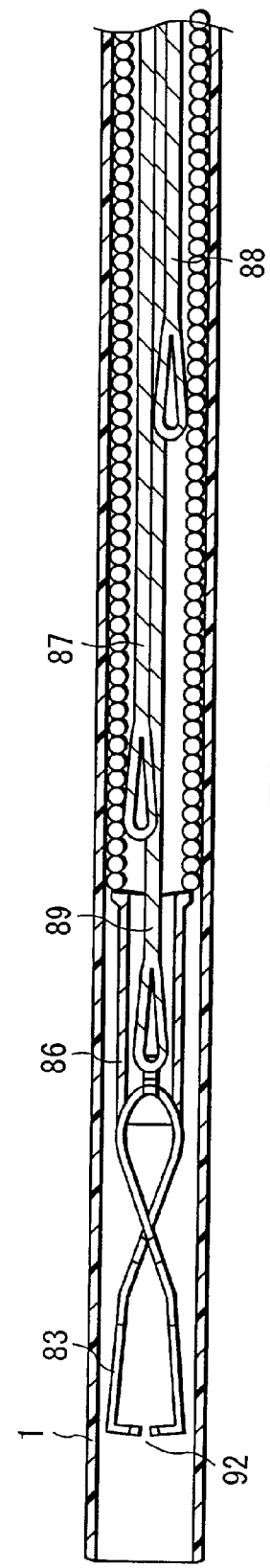
FIG. 14 is a longitudinal side section of a distal end portion of the device according to the present embodiment.

In order to continuously retain the clip 83 in the living tissue 100 in the body cavity, the manipulating wire 88 separated from the clip 82 is retracted to the internal cavity of the protruding member 4, as shown in FIG. 14. That is, the distal end of the manipulating wire 87 passes through the gap 92 between the pinch sections 3*c* and 3*c'* of the clip 83 and the inside of the clip tightening ring 86 in order, and reaches the internal cavity of the protruding member 4. The manipulating wire 88 separated from the clip 82 is thus retracted, whereby preparation for ligating the clip 83 has completed.

In this state, the introducing tube 1 is retracted to the proximal end side, and the clip 83 and clip tightening ring 86 are protruded from the introducing tube 1. A manipulation for ligating the clip 83 is completely identical to that for retaining the clip 82 in the living tissue 100. This makes it possible to retain the clip 83 in the living tissue 100.

Further, by repeating the same manipulation, a plurality of clips mounted in the introducing tube 1 can be retained in the living tissue 100 in a body cavity.

Now, a method for retracting the manipulating wires 87, 88, and 89 will be described here.

These three manipulating wires 87, 88, and 89 are guided to the internal cavity of the protruding member 4, are inserted into the internal cavity of the protecting pipe 30, and reaches the internal cavity 23*b* of the manipulating member slider 23. At the proximal end portions of he manipulating wires 87, 88, and 89, manipulating pipes 40*a*, 40*b*, and 40*c* are connected, respectively, as shown in FIG. 7B.

Further, at the proximal end portions of the manipulating pipes 40*a*, 40*b*, and 40*c*, knobs 41*a*, 41*b*, and 41*c* are connected, respectively, as shown in FIG. 7C. The manipulating pipes 40*a*, 40*b*, and 40*c* can be freely inserted into the internal cavity of the manipulating member slider 23 and the internal cavity of the slider seat 42. The knobs 41*a*, 41*b*, and 41*c* are engaged in the slits 42*a*, 42*b*, and 42*c* in the slider seat 42. In this manner, the knobs 41*a*, 41*b*, and 41*c* are retracted along the slits 42*a*, 42*b*, and 42*c*, whereby the manipulating wires 87, 88, and 89 can be independently retracted, respectively.

Now, a method for independently retracting the manipulating wires 2 respectively will be described to be associated with a manipulation of a manipulating section.

As shown in FIG. 10, a description will be given with respect to a state in which the introducing tube slider 22 is retracted, and the clip 81 and clip tightening ring 84 are protruded from the distal end of the introducing tube 1.

An action of expanding/opening the arm sections 3*b* and 3*b'* of the clip 81, an action of closing and ligating the arm sections 3*b* and 3*b'* of the clip 81, and an action of retaining the clip 81 in a living tissue are as follows.

A fixed handle 47*a* is pinched between a thumb and index finger, and four fingers from the index finger to a small finger are hooked on a sliding handle 47*c*. Then, the four fingers hooked on the sliding handle 47*c* are gripped. Then, the sliding handle 47*c* moves along a connecting bar, and then, moves to the fixed handle 47*a*. The sliding handle 47*c* is fixed to a manipulating section cover 45 via a sliding bolt 47*f*, and thus, the manipulating section cover 45 also moves to the fixed handle 47*a* due to the movement of the sliding handle 47*c*.

On the other hand, an engaging portion provided at the manipulating section cover 45 is in engagement with the knob 41*a* of the three knobs, as shown in FIG. 8E. A switch lever 46 having a knob engaging section 46*a* is fixed integrally with the manipulating section cover 45 via pins 46*b* and 46*c*, thus retracting the knob 41*a* in synchronism with the movement of the manipulating section cover 45. The knob 41*a* moves the inside of the slit 44*a* provided at the manipulating section 44, as shown in FIG. 15B.

That is, a manipulation for gripping the sliding handle 47*c* is carried out, thereby retracting the knob 41*a*. The knob 41*a* is connected to the distal end clip 81 via the manipulating pipe 40*a* and the manipulating wire 87. Thus, the clip 81 is retracted into the clip tightening ring 84 by retracting the knob 41*a*, and the arm sections 3*b* and 3*b'* of the clip 81 expand/open to the maximum.

In this state, the pinch sections 3*c* and 3*c'* of the clip 81 are pushed against the target living tissue 100. Further, the sliding handle 47*c* is further gripped, whereby the knob 41*a* is further retracted, the pinch sections 3*c* and 3*c'* of the clip 81 are closed, and the tissue can be pinched. The sliding handle 47*c* is further retracted, whereby the hook 3*f* provided at the proximal end portion 3*a* of the clip 81 is extended, and the clip 81 and manipulating wire 87 are disengaged from each other, thereby making it possible to retain the clip 81 in a living body.

After the clip 81 has been retained in the living tissue 100, when the sliding handle 47*c* is further retracted, the distal end of the manipulating wire 87 passes through the gap 91 between the pinch sections 3*c* and 3*c'* of the clip 82, the inside of the clip tightening ring 85, and then, the gap 92 between the pinch sections 3*c* and 3*c'* of the clip 83 and the inside of the clip tightening ring 86 in order, and is retracted back to the internal cavity of the protruding member 4. In this way, the manipulating wire 87 is retracted to the internal cavity of the protruding member 4, whereby preparation for ligating the clips 82 and 83 can be organized.

When a hand is released from the sliding handle 47*c*, the sliding handle 47*c* is pushed back forwardly, as shown in FIG. 17A, by means of biasing due to a spring 48 provided at the manipulating portion 44, and then, abuts against a handle stop 47*d*.

In order to ligate the clip 82, the jaw section 22*b* of the introducing tube slider 22 is gripped, and the introducing slider 22 is retracted to the proximal end side, as in the action for protruding the clip 81 from the introducing tube slider 22. At this time, an endoscopic image is well observed, and it is checked that the arm sections 3*b* and 3*b'* of the clip 82 are protruded from the distal end of the introducing tube 1.

Further, the introducing tube slider 22 is gradually retracted to a position in which the clip tightening ring 85 is protruded from the distal end of the introducing tube 1 by about 1 mm to 5 mm. At this time, care must be taken so that the arm sections 3*b* and 3*b'* of the clip 83 are not protruded from the distal end of the introducing tube 1. This is because, if the arm sections 3*b* and 3*b'* of the clip 83 are protruded, there is no means for controlling the clip 82, thus making it very difficult to reliably ligate the target living tissue 100.

While the clip 82 and clip tightening ring 85 are protruded from the introducing tube 1, the switch lever 46 is rotated, and the knob engaging section 46*a* is engaged with the knob 41*b*. Now, preparation for ligating the clip 82 has completed, as shown in FIG. 17C.

Subsequent manipulation is the same as an action of relating the clip 81. The knob 41b is retracted by retracting the sliding handle 47c. In this manner, the proximal end portion 3a of the clip 82 is retracted into the clip tightening ring 85, and the arm sections 3b and 3b' of the clip 82 expand/open to the maximum.

The sliding handle 47c is further retracted, whereby the hook 3f provided at the proximal end portion 3a of the clip 82 is extended, and the clip 82 and manipulating wire 88 are disengaged from each other, thus making it possible to retain the clip 82 in a living body. After the clip 82 has been retained in the living tissue 100, when the sliding handle 47c is further retracted, the distal end of the manipulating wire 88 passes through the gap 92 between the pinch sections 3b and 3b' of the clip 83 and the inside of the clip tightening ring 86 in order, and is retracted back to the internal cavity of the protruding member 4. In this way, the manipulating wire 88 is retracted to the internal cavity of the protruding member 4, whereby preparation for ligating the clip 83 can be organized, as shown in FIG. 14.

In order to ligate the clip 83, the jaw section 22b of the introducing tube slider 22 is gripped, and the introducing tube slider 22 is retracted to the proximal end portion as in the action of protruding the clip 82 from the introducing tube slider 22. At this time, an endoscopic image is well observed, and it is checked that the arm sections 3b and 3b' of the clip 83 are protruded from the distal end of the introducing tube 1.

Further, the introducing tube slider 22 is gradually retracted to a location at which the clip tightening ring 86 is protruded from the distal end of the introducing tube 1 by about 1 mm to 5 mm. At this time, care must be taken so that the protruding member 4 is not protruded from the distal end of the introducing tube 1. If the protruding member 4 is protruded, there is no means for controlling the clip 83, thus making it very difficult to reliably ligate the target living tissue 100.

While the clip 83 and clip tightening ring 86 are protruded from the introducing tube 1, the switch lever 46 is rotated, and the knob engaging section 46a is engaged with the knob 41c. Now, preparation for ligating the clip 83 has completed.

Subsequent manipulation is the same as the action of ligating the clip 82. The knob 41c is retracted by retracting the sliding handle 47c. In this manner, the proximal end portion of the clip 83 is retracted into the clip tightening ring 86, and the arm sections 3b and 3b' of the clip 83 expand/open to the maximum.

The siding handle 47c is further retracted, whereby the hook 3f provided at the proximal end portion 3a of the clip 83 is extended, and the clip 83 and manipulating wire 89 are disengaged from each other, making it possible to retain the clip 83 in a living body.

In this way, the three clip units 6 mounted in the introducing tube 1 can be retained in order in a living body cavity. The switch lever 46 is manipulated to be rotated, thereby making it possible to apply force to each of the plurality of manipulating wires 87, 88, and 89. Then, the force can be applied to each of the plurality of manipulating wires 87, 88, and 89 merely by gripping the sliding handle 47c. This makes it possible to ligate in order a plurality of clips 81, 82, and 83 mounted in the introducing tube 1.

According to the first embodiment described previously, the switch lever 46 is manipulated to be rotated, thereby making it possible to apply the force to each of the plurality of manipulating wires 2. Then, the force can be applied to each of the manipulating wires 2 merely by gripping the sliding handle 47c. In this manner, a surgeon can make ligating manipulation easily by selecting in order the plurality of clips 3 from the clip 3 mounted at the distal end of the introducing tube 1.

That is, the plurality of clips 3 mounted in the introducing tube 1 can be ligated in order merely by manipulating the switch lever 46 and handle 47. In this manner, the surgeon can use a multifunctional surgical operation device (living tissue clipping apparatus) including the plurality of clips 3 (surgical operation tools) efficiently without manipulating a complicated manipulating section. Thus, a surgical operation time can be reduced.

Now, a method for manufacturing the manipulating wire 2 will be described here.

As shown in FIG. 18, the manipulating wire 2 consists of a loop wire 2a and a proximal end wire 2b. The proximal end wire 2b is composed of a twisted metallic wire. For example, three element wires are twisted.

Now, a method for manufacturing the manipulating wire 2 (a manufacturing method using 1×3 twisted wires, for example) will be described with reference to FIG. 19A to FIG. 19J. The wire is about 0.3 mm to 0.6 mm in outer diameter.

1. A wire end portion 2c is loosened as shown in FIG. 19A.

2. One of the three wires, A, is loosened while turning it, as shown in FIG. 18B. At this time, a length of about 60 mm from the wire end portion 2c is loosened.

3. A second wire B or C is loosened similarly as shown in FIG. 19C. At this time, a length of about 60 mm from the wire end portion 2c is loosened similarly.

4. The second wire B or C is returned back as shown in FIG. 19D. At this time, a return end X and a loosened end Y must be well spaced from each other. In addition, during returning, a top portion when the wire is rounded should be folded as shown in the enlarged view.

5. The folded wire B is twisted by being turned in a loosening direction, as shown in FIG. 19E (in the case of Z twisting). At this time, a deformed portion of the end portion is cut before twisting. The twist back length is about 30 mm, as shown in FIG. 19F.

6. Wire C is twisted back to wire B, as shown in FIG. 19F, and the wire B is cut at a location of the return end. At this time, wires C and B must neither be spaced nor be superimposed. (Otherwise, the wire A is easily released when it is returned.)

7. The wire A is twisted back to the wire B or C, as shown in FIG. 19C. At this time, an abutment portion between the wires C and B may be observed under stereo-microscope. In addition, when the front or back side of the abutment portion is twisted, care must be taken so that the wires C and B do not move.

Further, as shown in FIG. 19H, when the wire A is loaded, care must be taken so that the wires B and C are not flapped in the direction indicated by the filled arrow. In addition, the wire A is easily loaded by placing it at the distal end side (loop side) relevant to the abutment portion between the wires B and C.

8. The wire A is cut at the extremity (indicated by a) of a loop, as shown in FIG. 19I.

9. The procedures have been completed as shown in FIG. 19J. A loop length is about 5 mm. In addition, the abutment portion between the wires B and C and the end portion of the wire A may be prevented from looseness of twist by a welding or adhesive method.

The thus constructed manipulating wire 2 is not increased in outer diameter at a bonding portion between the proximal end wire 2b and a loop wire 2a. Thus, the insert properties of the manipulating wire 2 is maintained without an increase in frictional resistance with an internal face of the introducing tube 1. In this manner, the clip 3 can be protruded from the introducing tube 1 more easily. In addition, the clip can be ligated with smaller force.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multifunctional surgical operation device comprising:
   a plurality of surgical operation tools;
   a plurality of manipulating members interlocked with the plurality of surgical operation tools and capable of independently manipulating the plurality of surgical operation tools each;
   a manipulating section capable of manipulating the plurality of manipulating members; and
   a switch lever mounted at the manipulating section and capable of being selectively engaged with the plurality of manipulating members, wherein only a surgical operation tool interlocked with the manipulating member engaged with the switch lever can be manipulated by manipulation of the manipulating section;
   wherein the manipulating member comprises a manipulating wire movably inserted into the introducing tube, and the surgical operation tools are connected to a distal end of the manipulating wire.

2. A device according to claim 1, wherein the plurality of surgical operation tools are movably inserted into an introducing tube capable of being inserted into a living body cavity.

3. A device according to claim 1, wherein the switch lever can rotate relevant to the manipulating section.

4. A device according to claim 1, wherein the number of the surgical operation tools is three or more, and the switch lever can be selectively engaged with three or more manipulating members.

5. A multifunctional surgical operation device comprising:
   a plurality of surgical operation tools;
   a plurality of manipulating members interlocked with the plurality of surgical operation tools and capable of independently manipulating the plurality of surgical operation tools each;
   a manipulating section capable of manipulating the plurality of manipulating members; and
   a switch lever mounted at the manipulating section and capable of being selectively engaged with the plurality of manipulating members, wherein only a surgical operation tool interlocked with the manipulating member engaged with the switch lever can be manipulated by manipulation of the manipulating section;
   wherein the plurality of surgical operation tools are composed of identical tools.

6. A device according to claim 5, wherein the tools are composed of clips capable of ligating a living tissue.

7. A device according to claim 6, wherein the clips each have a proximal end portion, a pinch section is formed at a distal end of an arm section extending from the proximal end portion, and opening/expanding properties are imparted.

8. A device according to claim 7, wherein there is provided a clip tightening ring engagingly mounted on the arm section of the clip, thereby closing the pinch section of the clip.

9. A device according to claim 8, wherein there is provided a protruding member movably inserted into the introducing tube in close proximity to the clip tightening ring arranged at the most proximal end portion of the introducing tube.

10. A device according to claim 5, wherein the plurality of surgical operation tools are movably inserted into an introducing tube capable of being inserted into a living body cavity.

11. A device according to claim 5, wherein the manipulating member comprises a manipulating wire movably inserted into the introducing tube, and the surgical operation tools are connected to a distal end of the manipulating wire.

12. A device according to claim 5, wherein the switch lever can rotate relevant to the manipulating section.

13. A device according to claim 5, wherein the number of the surgical operation tools is three or more, and the switch lever can be selectively engaged with three or more manipulating members.

* * * * *